United States Patent
Wang et al.

(10) Patent No.: US 11,638,567 B2
(45) Date of Patent: *May 2, 2023

(54) SIMULTANEOUS INTERIOR MRI AND X-RAY IMAGING SYSTEM (MRX)

(71) Applicant: Rensselaer Polytechnic Institute, Troy, NY (US)

(72) Inventors: Ge Wang, Loudonville, NY (US); Lars Arne Gjesteby, Cohasset, MA (US)

(73) Assignee: Rensselaer Polytechnic Institute, Troy, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/679,716

(22) Filed: Feb. 24, 2022

(65) Prior Publication Data
US 2022/0175329 A1    Jun. 9, 2022

Related U.S. Application Data

(63) Continuation of application No. 15/775,906, filed as application No. PCT/US2016/061890 on Nov. 14, 2016, now Pat. No. 11,278,250.

(60) Provisional application No. 62/254,773, filed on Nov. 13, 2015.

(51) Int. Cl.
| | |
|---|---|
| *A61B 6/00* | (2006.01) |
| *A61B 5/055* | (2006.01) |
| *G01R 33/381* | (2006.01) |
| *G01R 33/383* | (2006.01) |
| *G01R 33/48* | (2006.01) |
| *A61B 5/00* | (2006.01) |
| *A61B 6/02* | (2006.01) |
| *A61B 6/03* | (2006.01) |

(52) U.S. Cl.
CPC .......... *A61B 6/4417* (2013.01); *A61B 5/0035* (2013.01); *A61B 5/055* (2013.01); *A61B 6/027* (2013.01); *A61B 6/032* (2013.01); *A61B 6/5247* (2013.01); *G01R 33/381* (2013.01); *G01R 33/383* (2013.01); *G01R 33/4812* (2013.01); *A61B 6/5217* (2013.01)

(58) Field of Classification Search
None
See application file for complete search history.

(56) References Cited

U.S. PATENT DOCUMENTS 11,278,250 B2 * 3/2022 Wang .................. A61B 6/4417

* cited by examiner

*Primary Examiner* — David P Porta
*Assistant Examiner* — Mamadou Faye
(74) *Attorney, Agent, or Firm* — Murtha Cullina LLP; Anthony P. Gangemi (57) ABSTRACT

Systems and methods for obtaining simultaneous X-ray—magnetic resonance imaging (MRI) images are provided. A magnetic resonance X-ray CT (MRX) system can combine X-ray imaging and MRI in a cost-effective and relatively simple solution for improved imaging. During imaging of a subject, the X-ray source and X-ray detector can be simultaneously rotated around the subject, and the means for generating a magnetic field can also be rotated around the subject. The means for generating a magnetic field can be a plurality of permanent magnets.

28 Claims, 7 Drawing Sheets

SIMULTANEOUS INTERIOR MRI AND X-RAY IMAGING SYSTEM (MRX)

CROSS REFERENCE TO RELATED APPLICATION(S)

This application is a continuation application of and claims priority benefit of co-pending U.S. patent application Ser. No. 15/775,906, filed May 14, 2018, which claims priority benefit of International Patent Application No. PCT/US2016/061890, filed Nov. 16, 2016, which claims priority benefit of U.S. Provisional Patent Application No. 62/254,773, filed Nov. 13, 2015, the contents of which are incorporated herein by reference in their entirety, including any figures, tables, and drawings.

BACKGROUND

According to the National Center for Health Statistics, heart and oncologic diseases are the top two causes of mortality in the United States. Considerable strides have been made in imaging of these maladies with technologic innovations in X-ray imaging, computed tomography (CT), magnetic resonance imaging (MRI), single photon emission computed tomography/positron emission tomography (SPECT/PET), ultrasound, and optical imaging including optical coherence tomography (OCT) and fluorescence imaging. These imaging modalities are routinely used worldwide, producing critical tomographic information of the human body and enabling evaluation of not only anatomical and functional features but also cellular and molecular features in modern medicine. However, each individual imaging modality has its own contrast mechanism with strengths and weaknesses, and imaging protocols depend on many interrelated factors. Both individual (CT, MRI, PET, and SPECT) and hybrid modalities (PET/SPECT-CT and PET/MRI) are clinically accepted with strong evidence of healthcare benefits.

Each tomographic modality has distinct advantages, including high temporal and spatial resolution with CT, excellent tissue characterization and nonionizing radiation with MRI; and high sensitivity for molecular imaging with SPECT or PET. However, no single modality is sufficient to depict the complex dynamics of mammalian physiology and pathology. As evidenced by SPECT-CT and PET-CT scanners, modality fusion imaging can be effective and synergistic and has had tremendous impact on both experimental discovery and clinical care. Even with current multi-modality imaging, though, limitations exist, including reconstruction techniques that are inefficient and/or inaccurate.

SUMMARY

Embodiments of the subject invention provide novel and advantageous systems and methods for obtaining and/or reconstructing simultaneous X-ray (e.g., X-ray computed tomography (CT))—magnetic resonance imaging (MRI) images. A magnetic resonance X-ray CT (MRX) system can combine X-ray imaging and MRI in a cost-effective and relatively simple solution for improved imaging. The system can include spiral X-ray imaging along with MRI.

In an embodiment, a system for performing simultaneous X-ray imaging and MRI can include an X-ray source, an X-ray detector for detecting X-rays from the X-ray source, a radio frequency (RF) coil, at least one gradient coil, and means for generating a magnetic field for MR imaging. The system can be configured such that, during imaging of a subject, the X-ray source and X-ray detector are simultaneously rotated around the subject and the means for generating a magnetic field is rotated around the subject. The X-ray source, the X-ray detector, and the means for generating a magnetic field can also be translated longitudinally along a region of interest of the subject during imaging of the subject. The means for generating a magnetic field can be, for example, a plurality of permanent magnets.

In another embodiment, a system for performing simultaneous X-ray imaging and MRI is provided including an X-ray source, and X-ray detector for detecting X-rays from the X-ray source, a radio frequency (RF) coil, at least one gradient coil, and a magnetic field source for MR imaging. The magnetic field source includes a first magnet ring and a second magnet ring disposed such that their radii are substantially parallel to each other. The magnetic field source includes a partial third magnet ring disposed between the first and second magnet rings in an axial direction substantially perpendicular to the radii of the first and second magnet rings such that the partial third magnet ring is not concentric to either of the first magnet ring and the second magnet ring. The system is configured such that, during imaging of a subject, the X-ray source and X-ray detector are simultaneously rotated around the subject, and the magnetic field source is rotated around the subject.

DETAILED DESCRIPTION

Embodiments of the subject invention provide novel and advantageous systems and methods for obtaining and/or reconstructing simultaneous X-ray (e.g., X-ray computed tomography (CT))—magnetic resonance imaging (MRI) images. A magnetic resonance X-ray CT (MRX) system can combine X-ray imaging and MRI in a cost-effective and relatively simple solution for improved imaging. The system can include spiral X-ray imaging along with MRI.

In many embodiments, simultaneous CT and MR views can be acquired for hybrid radiographic imaging or joint tomographic reconstruction. Configurations using permanent magnet can achieve a magnetic field strength of, for example, between 0.1 and 0.2 Tesla (T) while keeping weight low enough for portability. A field strength of, for example, 0.35 T can be achieved with permanent magnets that maintain a compact profile, though increased weight can make transportation more difficult than with lighter magnets. An MRX system as described herein can perform double helical scans in CT and MRI mechanisms, and can have multiple applications, including but not limited to medical imaging on disaster sites, in battle fields, and for underdeveloped regions.

Major challenges with the fusion of CT and MRI include the size conflict between hardware components and electromagnetic interferences, such as the magnetic field-induced electron deflection in the X-ray tube. However, low-field MRI minimizes the fringe magnetic field that affects X-ray components and is viable for producing clinically useful images. Furthermore, compressed sensing and interior tomography principles enable the use of smaller hardware components and fewer projections for local image reconstruction, which facilitates simultaneous CT-MRI.

Projection-based conventional X-ray radiography has wide-ranging applications in modern medical practice. It has come to represent an indispensable part of patient work-up spanning from acute to chronic conditions and cancers, as well as from infectious to trauma-related applications. The low cost, low radiation dose, widespread availability, and rapid, often bedside acquisition have made it the most commonly used imaging technique over the past 100 years. Despite these advantages, conventional radiography on its own remains a modality with two-dimensional projection data from a three-dimensional anatomy, as well as one with significantly limited soft tissue contrast resolution. Other cross-sectional imaging techniques such as CT and MRI have 3D capabilities and superior contrast resolution. While CT scanning is associated with higher radiation dose as compared to conventional radiography, the volumetric capability is greatly beneficial. MRI does not involve any ionizing radiation and delivers superior contrast resolution compared to CT. However, unlike CT, the application of MR for determining fracture fragments and their alignment cannot be reliably obtained. These individual shortcomings make the harmonization of CT and low-strength MRI highly attractive.

Fahrig et al. previously attempted to combine an X-ray tube and an MRI scanner ("A truly hybrid interventional MR/X-ray system: Feasibility demonstration," J. Magn. Reson. Imaging, vol. 13, no. 2, pp. 294-300, 2001; which is hereby incorporated herein by reference in its entirety), but embodiments of the subject invention can employ simultaneous spiral CT and MRI to achieve hybrid radiographic imaging and joint tomographic reconstruction. Smaller scale designs can be used for the MRX system and can acquire simultaneous views using spiral CT in combination with spiral MRI (e.g., spiral low-field MRI). Spiral scanning is preferred due to its ability to acquire higher quality images for a given level of radiation dose or a given size of a dataset (Wang et al., "Low-contrast resolution in volumetric x-ray CT—analytical comparison between conventional and spiral CT," Med. Phys., vol. 24, no. 3, pp. 373-376, 1997; which is hereby incorporated herein by reference in its entirety).

In many embodiments, an MRX scanner can be specifically designed for head and extremities imaging to reduce the cost and dimensions of the magnet. A compact profile can allow for ease of transportation while enabling high-quality images over regions of interest (ROI). The means for generating the main magnetic field needed for MRI can be, for example, one or more permanent magnets, one or more superconducting magnets, and/or one or more resistive magnet coils. For example, permanent magnets can be used as the primary means for generating the main magnetic field needed for MRI and can be used in one or more Halbach configurations that achieve various patterns of homogeneous magnetic fields by radial polarization arrangements of magnet blocks. Halbach et al. ("Physical and Optical Properties of Rare Earth Cobalt Magnets for Particle Optics," Nucl. Instruments Methods, pp. 1-10, 1981; which is hereby incorporated herein by reference in its entirety) and Bjork et al. ("Optimization and improvement of Halbach cylinder design," J. Appl. Phys., vol. 104, no. 1, pp. 1-9, 2008; which is hereby incorporated herein by reference in its entirety) both discuss Halbach configurations.

Halbach configurations of permanent magnets can maximize the field at the center of the blocks while minimizing the field outside. Permanent magnets are less expensive than the superconducting magnets employed in the standard clinical units, which require liquid nitrogen or helium maintained at extremely cold "critical" temperatures to nullify the electrical resistance of the wire. This complexity does not facilitate movability, and operation costs are high. Because permanent magnets have an always-present magnetic field and do not need a power source to generate the field, they are much easier to maintain while the only obstacle to mobility is weight of the material. Another potential drawback of permanent magnets is that the field cannot be shut off so ferromagnetic metal would have to be kept away from the scanner. Simple resistive magnet coils are a potential alternative to both permanent and superconducting magnets, as they are less expensive than superconductors, and their field can be shut off. However, the high amount of current needed to generate clinically relevant fields makes resistive magnets potentially less desirable than permanent magnets.

The simultaneous, compact spiral CT-MRI systems and methods of embodiments of the subject invention have several applications. A major application is for assessing trauma, specifically of the extremities, spine, or head, so that images can be acquired rapidly with minimal patient movement. MRX is also a way to bring medical imaging to developing countries that do not have wide access to hospital-grade equipment. An inexpensive, compact scanner that performs both CT and MRI can bring essential help to regions that have been without either of them thus far.

A discussion of the physical principles involved X-ray imaging and MRI follows. In digital radiography, X-ray photons are directed from an X-ray source (e.g., X-ray tube) toward an object of interest and are absorbed, scattered, or transmitted to a detector (e.g., detector array). For example, a flat panel detector array measures the intensity of X-rays received at each pixel, and converts this quantity into light or an electrical signal. The digital output resulting from the analog signal can be used to form raw data. Spiral CT acquires views at many angles as the source rotates around the subject (e.g., patient) being translated into the gantry. The hardware involved can be considered relatively straightforward compared to MRI.

Typical clinical MRI scanners contain a magnet with a field strength in the range of 1 T to 3 T. In humans, the spins targeted by MRI systems are in the hydrogen protons. When the spins are in the magnetic field of a scanner, they tend to be aligned along the axis of the field. The hydrogen atoms can orientate either parallel or antiparallel to the main field direction, and there will be slightly more spins lined up in the parallel direction, creating a net magnetization vector. The magnetization vector processes around the field axis as a frequency ($\omega_0$) that is dependent on the strength of the magnetic field ($\beta_0$) and the constant gyromagnetic ratio ($\gamma$):

$$\omega_0 = \gamma \beta_0 \quad (1)$$

To perturb this precession, a radio frequency (RF) pulse at the resonant frequency, known as the Larmor frequency, of the hydrogen protons can be applied to an area of the body to be imaged. The gyromagnetic ratio for hydrogen is 42.57 MegaHertz per Tesla (MHz/T), so the Larmor frequency of hydrogen protons in a 1 T field is 42.57 MHz. Typically, the RF pulse is shut off when the magnetization vector falls 90° from the original direction. After this point, the hydrogen atoms relax back to their steady state in the magnetic field. During this relaxation, energy released by the protons results in a signal that can be detected by the RF coil.

MRI images are formed by pinpointing the spatial location of proton groups that are spinning at different rates. To achieve this, gradient coils can be employed in combination for slice selection, frequency encoding, and phase encoding. When turned on, the gradient coils alter the strength of the homogeneous main magnetic field linearly along the x-, y-, and/or z-directions so that protons process at various frequencies within different time windows depending on their locations in the gradient field. An alternative method for encoding is to instead take advantage of slight non-uniformities in the main magnetic field so that field strength naturally varies with location in the imaging field of view, which can eliminate some hardware. Either way, the signals acquired by the RF coil give information in the Fourier domain for image reconstruction. The principle of interior tomography enables small regions of interest to be reconstructed with less data than necessary for global reconstruction. For MRI, this means that the homogeneous magnetic field area can be focused only on a specific region to be imaged.

MRX systems of embodiments of the subject invention can have the following advantageous characteristics: low weight for portability, low power for efficiency, a homogeneous main magnetic field over the imaging region, a clinically-relevant main magnetic field strength, and minimal fringe fields. To achieve these characteristics, certain system components can be present (e.g., in certain configurations).

The main magnetic field for clinical MRI is typically generated by superconducting magnets. When cooled to a critical temperature, these coils have zero electrical resistance and can carry high current density. This allows for a high magnetic field to be efficiently achieved. Despite these advantages, superconducting magnets are expensive to build and require liquid nitrogen or helium. In addition, they typically weigh several thousand kilograms. While superconducting magnets are the best option for generating the ideal magnetic field, they prohibit portability and are inhibit production of a low-cost, compact MRX system. Certain embodiments of the subject invention may use superconducting magnets to obtain a very good magnetic field, but they result in larger size, decreased portability, and increased cost.

In some embodiments of the subject invention, permanent magnets and/or resistive magnets can be used as the means for generating the main magnetic field. Permanent magnets for MRI have the advantage over electromagnets of not needing an electric current. The material of the magnet can be, for example, a rare-earth metal, and can produce an ever-present field, thus removing power consumption and thermal dissipation concerns for the system. In certain embodiments, the maximum field strength in the MRX system can be kept to 0.2 T or about 0.2 T to minimize fringe fields and reduce interference with the X-ray components. In many embodiments, the means for generating the main magnetic field can be permanent magnets in a Halbach array. The Halbach array(s) can be designed to produce a strong field at the center of the magnet configuration while keeping the external fringe field low.

In certain embodiments, the maximum field strength in the MRX system can be, for example, any of the following values, about any of the following values, at least any of the following values, at least about any of the following values, not more than any of the following values, not more than about any of the following values, or within any range having any of the following values as endpoints (with or without "about" in front of one or both of the endpoints), though embodiments are not limited thereto (all numerical values are in Tesla (T)): 0.0001, 0.001, 0.0034, 0.0035, 0.0064, 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.25, 0.30, 0.35, 0.40, 0.50, 0.60, 0.70, 0.80, 0.90, or 1.0. For example, the maximum field strength in the MRX system can be 0.35 T or less.

Resistive magnets are electromagnets through which a strong electric current can flow in a coil. A magnetic field inside the coil is proportional to the intensity of the electric current supplied. The field can be removed by turning off the power supply. Despite this advantage, large amounts of current are needed to achieve clinically relevant field strengths. The material and design of the coil can be altered for various field strengths, such as by wrapping a wire around an iron core instead of a hollow container, or constructing a Bitter magnet solenoid. Bitter magnets are built by stacking circular copper plates in a helical configuration with insulating spacers (Bird et ah, "Design of the next generation of Florida-bitter magnets at the NHMFL," IEEE Trans. Appl. Supercond., vol. 14, no. 2, pp. 1253-1256, 2004; which is hereby incorporated herein by reference in its entirety). Because all resistive magnets consume power and generate heat, cooling systems must be integrated. Bitter plates are designed with many holes to allow water to circulate through the stack to control temperature. Although these engineering adjustments improve the viability of resistive magnets, permanent magnets can result in greater portability and lower cost. If zero resistance of superconducting coils could be achieved at higher temperatures without the need for cryogenic cooling, then resistive magnets would be more advantageous.

Embodiments, of the subject invention can provide a portable imaging unit with the ability to simultaneously acquire an X-ray image and an MRI image. Thus, X-ray radiography with MR can be used to assess fractures, bone contusions, and internal bleeding directly on a natural disaster field or at a patient's bedside. Such a system will require a power source, and an onboard power source can lend to the portability of the system. In an embodiment, such a system can be powered by an onboard supercapacitor array to facilitate mobility. A patient in critical condition would therefore not have to be transported to an imaging suite, and MRX could remove the need for a higher-dose CT exam and a subsequent independent MRI, allowing for faster treatment decisions.

Commercially available supercapacitors can be used as energy storage banks for MRI scanners (Ristic et al., "Supercapacitor Energy Storage for Magnetic Resonance Imaging Systems," Ind. Electron. IEEE Trans., vol. 61, no. 8, pp. 4255-4264, 2014; which is hereby incorporated herein by reference in its entirety). Various pulse sequences have been successfully tested with supercapacitors, including T1 and 72 spin echoes. Graphene supercapacitors are a developing technology with the highest charge-capacity-to-weight ratio up to 550 Farads per gram (F/g). This characteristic is due to its single atomic layer makeup, leading to a high relative surface area for storing charge while minimizing thickness. A supercapacitor can build upon the graphene technology and incorporate nitrogen doping of the carbon layers for higher energy storage while maintaining rapid charging and discharging rates; such a material can achieve a capacitance of 855 F/g in aqueous electrolytes (Lin et al., "Nitrogen-doped mesoporous carbon of extraordinary capacitance for electrochemical energy storage," Science., vol. 350, no. 6267, pp. 1508-1513, December 2015; which is hereby incorporated herein by reference in its entirety). The cost and power requirement of a supercapacitor array is dependent on the type of magnets used in the system and the field strength needed. Because resistive magnets consume the most power of all magnet types, using permanent magnets as the means for generating the main magnetic field can substantially lessen the load. In such as case, the power source would only need to support X-ray components, MRI gradient coils, circuitry, and possibly one or more computers.

In some embodiments, an MRX system can include electromagnetic shielding. An electromagnetic shield can be present to provide shielding of the magnetic field beyond the region where it is needed to minimize interference with X-ray production. For example, a support structure made of a ferromagnetic material, such as steel, can be present, through which the magnetic field generated by the electromagnet can complete its path. With steel blocks located at the bottom of the permanent magnet rings, the residual field can be attracted to this material and minimize the leakage at the top of the gantry.

In MRX systems according to many embodiments of the subject invention, the X-ray (e.g., X-ray CT) and MRI subsystems can perform measurements simultaneously. Because CT and MRI are hardware-wise independent, image reconstructions can be independently performed in a manner similar to conventional CT and MRI as the bottom line. Further, given the spatially and temporally registered CT and MR measurements obtained by MRX, a combined image reconstruction scheme can benefit both sub-system performances. Xi et al. ("Simultaneous CT-MRI Reconstruction for Constrained Imaging Geometries using Structural Coupling and Compressive Sensing," IEEE Trans. Biomed. Eng., vol. 63, no. 6, pp. 1301-1309, 2016; which is hereby incorporated herein by reference in its entirety; and "United iterative reconstruction for spectral computed tomography," Med. Imaging, IEEE Trans., vol. 34, no. 3, pp. 769-778, 2015; which is hereby incorporated herein by reference in its entirety) and Wang et al. (International Patent Application No. PCT/US2016/051755) discuss methods for reconstruction of CT and MRI subsystems.

In embodiments of the subject invention, a unified CT-MRI image reconstruction scheme can be adapted to lower the radiation dose of CT and improve the image quality of MRI with a low background magnetic field. The CT-MRI reconstruction method can be a learning-based method, which learns the relationships between low-resolution CT (or MRI) images and high-resolution CT (or MRI) images.

The first step is to reconstruct CT and MRI images, for example using the simultaneous algebraic reconstruction technique with total variation (SART-TV):

$$\min_{u_{CT}} \|u_{CT}\|_{TV}, \text{ s.t. } Mu_{CT} = f, \text{ and} \tag{2}$$

$$\min_{u_{MRI}} \|u_{MRI}\|_{TV}, \text{ s.t. } RFu_{MRI} = g, \tag{3}$$

where $u_{CT}$ and $u_{MRI}$ are respectively CT and MR images to be reconstructed, M is a system matrix in CT imaging, F denotes the Fourier transform, R is a sampling mask in the k-space, f and g are CT and MRI measurements, respectively, and $\|\cdot\|_{TV}$ denotes the TV transformation.

Structural coupling and compressive sensing techniques can be combined, in which each sub-image in CT (or MRI) is represented by paired local CT-MRI structures. That is, the association between target CT and MRI images can be naturally established. In the joint image reconstruction, such an association can be extracted using an artificial neural network to guide both CT and MRI reconstructions:

$$\min_{u_{CT}} (1-\alpha)\|u_{CT}\|_{TV} + \alpha\|u_{CT} - u_{CT}^{est}\|_{TV}, \text{ s.t. } Mu_{CT} = f, \text{ and} \quad (4)$$

$$\min_{u_{MRI}} (1-\alpha)\|u_{MRI}\|_{TV} + \alpha\|u_{MRI} - u_{MRI}^{est}\|_{TV}, \text{ s.t. } RFu_{MRI} = g, \quad (5)$$

where $u_{CT}^{est}$ and $u_{MRI}^{est}$, are estimated images using the CT-MRI artificial neural network according to the corresponding CT and MRI images, respectively, a balances contributions from total variation and image similarity, respectively. Equations (2)-(5) are all well-posed convex optimization problems. These equations can be effectively solved, for example, in the split-Bregman framework.

The detailed implementation of a unified CT-MRI reconstruction scheme is discussed in Xi et al. (referred to above). These algorithms can handle a small degree of inhomogeneity in the Bo magnetic field by utilizing the interior MRI reconstruction technique, which looks for regions of equal field strength ("level sets") and sufficient gradient to achieve spatial localization. The region of interest can be reconstructed solely with data inside that region, and an accurate solution can be obtained. If the local magnetic field is made homogeneous, interior MRI can be even easier with conventional gradient and RF coils.

Figure 1A:
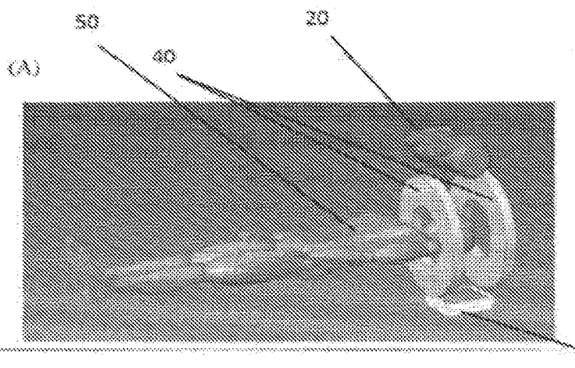
FIG. 1A shows a schematic view of a combined magnetic resonance imaging (MRI)—X-ray imaging (MRX) system according to an embodiment of the subject invention.

FIG. 1A shows a schematic view of a combined magnetic resonance imaging (MRI)—X-ray imaging (MRX) system according to an embodiment of the subject invention. Referring to FIG. 1A, the system can include an X-ray source 20, an X-ray detector 30, and a means 40 for generating the magnetic field for the MR imaging. The means 40 can be, for examples a plurality of permanent magnets. FIG. 1A shows two magnet rings positioned with their radii generally parallel to each other, and the X-ray source 20 and detector 30 can be positioned such that the X-rays are provided between the two magnet rings. The subject 50 to be imaged can be positioned within the magnet rings and between the X-ray source 20 and detector 30 during imaging.

Figure 1B:
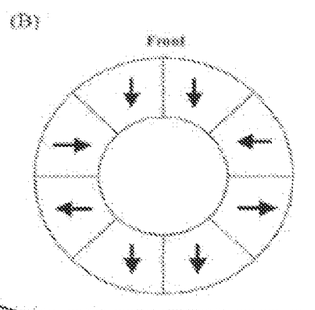
FIG. 1B shows a cross-sectional view of a magnet ring that can be used with an MRX system according to an embodiment of the subject invention.

FIG. 1B shows an example of the magnet rings; one or both of the magnet rings can have the configuration shown in FIG. 1B, which is only provided for exemplary purposes and should not be construed as limiting. Referring to FIG. 1B, one or both magnet rings may include eight permanent magnets, and the orientation of the permanent magnets within the ring can be as shown.

Figure 1C:
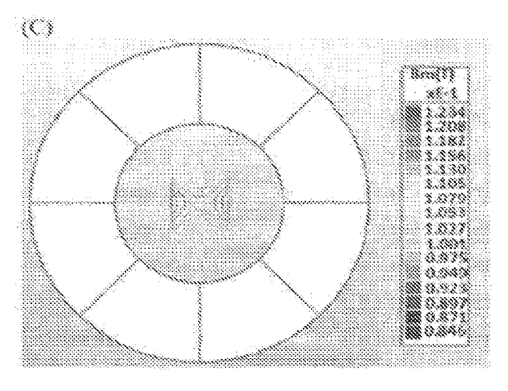
FIG. 1C shows a view of the magnetic field produced by a magnet ring that can be used with an MRX system according to an embodiment of the subject invention.
Figure 1D:
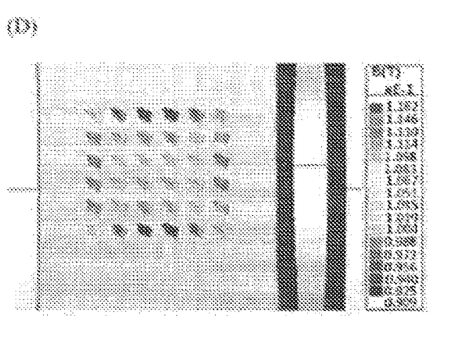
FIG. 1D shows a view of the magnetic field arrows in a cubic region to be imaged, as seen from a side view between two rings in an MRX system according to an embodiment of the subject invention.
Figure 1E:
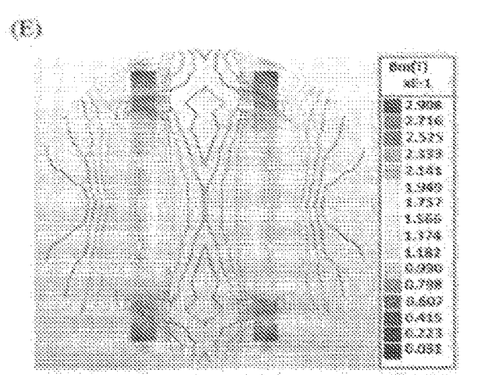
FIG. 1E shows a side view of the fringe magnetic field around the gantry in an MRX system according to an embodiment of the subject invention, without steel return blocks at the bottom.
Figure 1F:
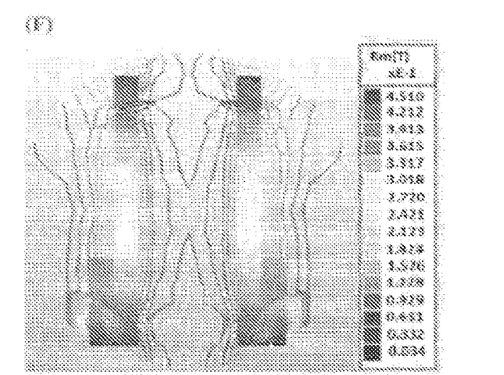
FIG. 1F shows a side view of the fringe magnetic field around the gantry in an MRX system according to an embodiment of the subject invention, with steel return blocks at the bottom.
Figures 1G, 1H:
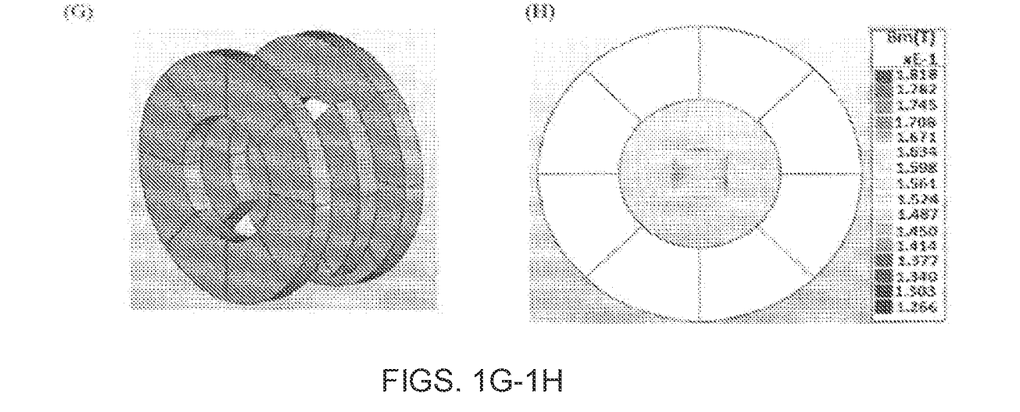
FIG. 1G shows a schematic view of magnet rings, including a partial third ring, which can be used with an MRX system according to an embodiment of the subject invention.
FIG. 1H shows a view of the magnetic field produced by the magnet ring of FIG. 1G.

FIG. 1G shows a schematic view of magnet rings, including a partial third ring, which can be used with an MRX system according to an embodiment of the subject invention. Referring to FIG. 1G, a partial third ring can be added between the two magnet rings, based on the system shown in FIG. 1A, with each magnet ring having the configuration shown in FIG. 1B. The partial magnet ring can include, for example, only four magnet blocks, such as the four side magnet blocks, such that space for the X-ray components can be preserved. Such a partial third ring can increase the magnetic field strength, which can thereby improve the imaging quality. The partial third ring shown in FIG. 1G is shown for exemplary purposes only and should not be construed as limiting. Other configurations of a third (or fourth, or fifth, etc.) ring can be included, partial or complete, to increase the magnetic field while also ensuring that the X-ray source and X-ray detector maintain line of sight and can be simultaneously used with the MR subsystem for imaging of the subject. As more magnet blocks or rings are added, the weight and cost increases and portability decreases, so there is a tradeoff.

Figures 2A, 2B, 2C:
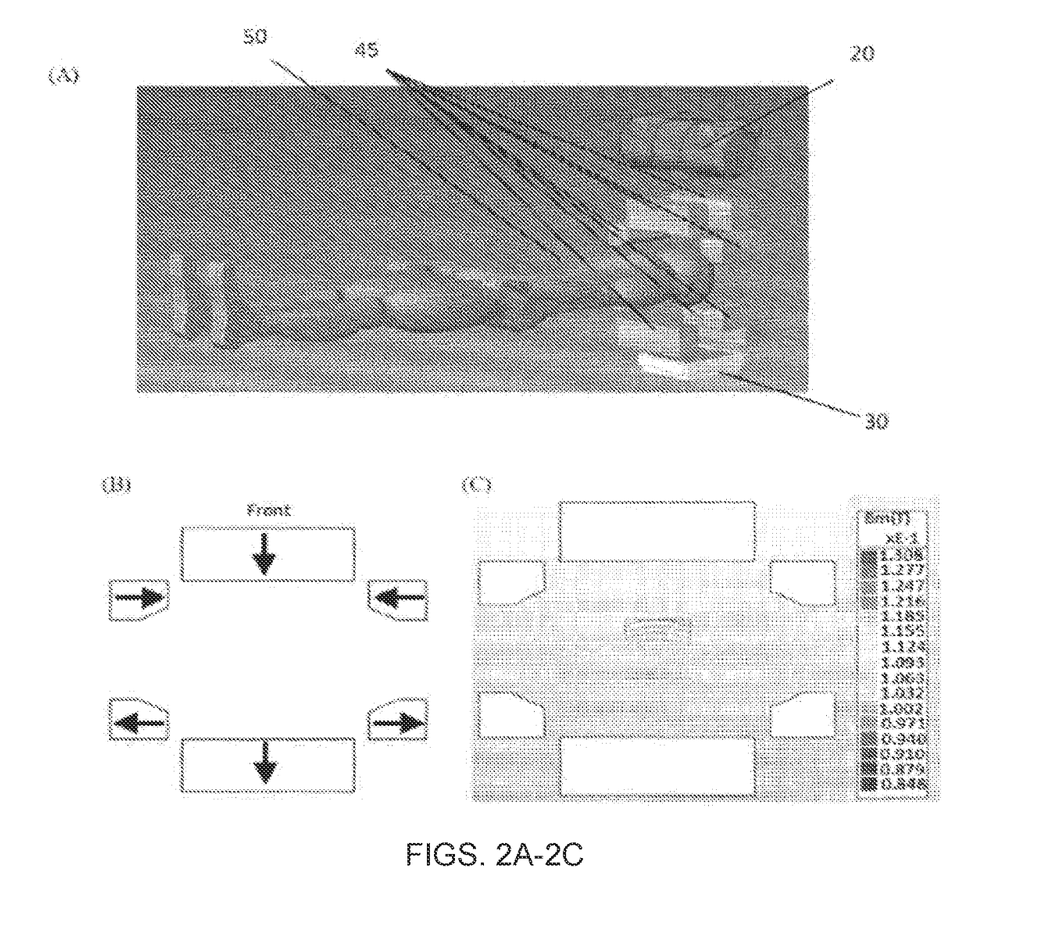
FIG. 2A shows a schematic view of an MRX system according to an embodiment of the subject invention.
FIG. 2B shows a cross-sectional view of a bar magnet arrangement that can be used with an MRX system according to an embodiment of the subject invention.
FIG. 2C shows a view of the magnetic field produced by a bar magnet arrangement that can be used with an MRX system according to an embodiment of the subject invention.

FIG. 2A shows a schematic view of a MRX system according to an embodiment of the subject invention. Referring to FIG. 2A, the system can be similar to that shown in FIG. 1A, but the means 45 for generating the magnetic field for the MR imaging can be, for examples a plurality of permanent magnets in the form of a bar arrangement. FIG. 2A shows eight magnet bars positioned generally between the X-ray source 20 and detector 30, such that the X-rays from the source 20 are provided between the magnet bars. The subject 50 to be imaged can be positioned within the magnet bars and between the X-ray source 20 and detector 30 during imaging.

FIG. 2B shows an example of the magnet bars (front view); the back magnet bars not shown in this cross-sectional view can have the same polarity as the magnets in front of them in the view (e.g., down as depicted in FIG. 2B), can have different polarity than these magnets, or one can have the same polarity and the other can have different polarity as the magnet in front of it as depicted in FIG. 2B. The configuration in FIG. 2B is only provided for exemplary purposes and should not be construed as limiting.

In both FIGS. 1A and 2A, the gradient coils and radio frequency (RF coil) needed for MRI are omitted for visual simplicity, but these would also be present in the system surrounding the subject 50.

Each permanent magnet can include, for example, a rare earth metal. For example, any or each permanent magnet can include neodymium ferrite boron (NdFeB), such as NdFeB 45 MGOe Sintered.

Figures 4A, 4B, 4C:
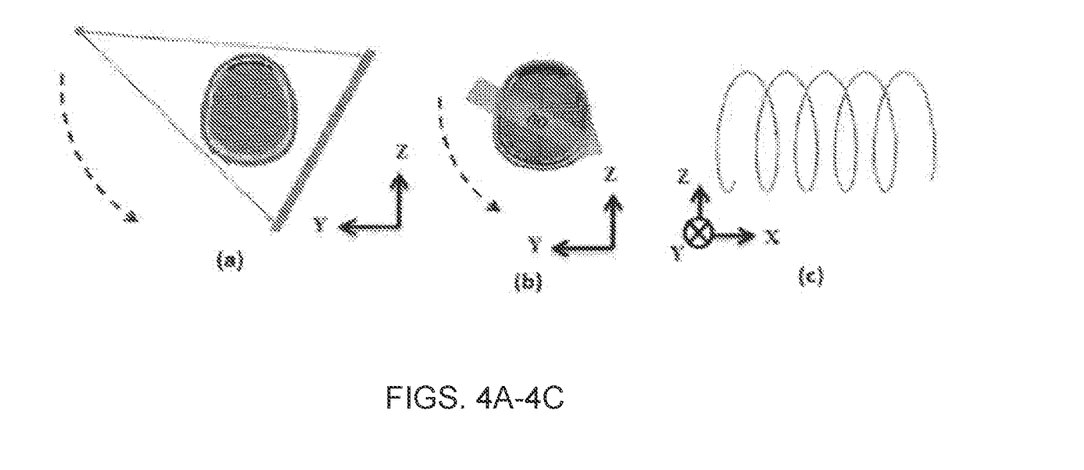
FIG. 4A shows a schematic view of data acquisition with an MRX system according to an embodiment of the subject invention, illustrating an X-ray source and detector being rotated around a subject.
FIG. 4B shows a schematic view of data acquisition with an MRX system according to an embodiment of the subject invention, illustrating rotation of an MR gantry around the subject to achieve a spatial encoding magnetic field to obtain generalized projection data.
FIG. 4C shows a schematic view of data acquisition with an MRX system according to an embodiment of the subject invention, illustrating longitudinal translation of the system during X-ray (e.g., CT X-ray) and MRI data acquisition.

FIGS. 4A-4C show schematic views of data acquisition with an MRX system according to an embodiment of the subject invention. FIG. 4A illustrates an X-ray source and detector being rotated around a subject. FIG. 4B illustrates rotation of an MR gantry around the subject to achieve a spatial encoding magnetic field to obtain generalized projection data. FIG. 4C illustrates longitudinal translation of the system during X-ray (e.g., CT X-ray) and MRI data acquisition, which results in a helical pattern when combined with the rotation. One or both subsystems can rotate and translate longitudinally, and in the case of both doing so, double helical scanning trajectories can be obtained to cover a long region of interest.

Figure 7:
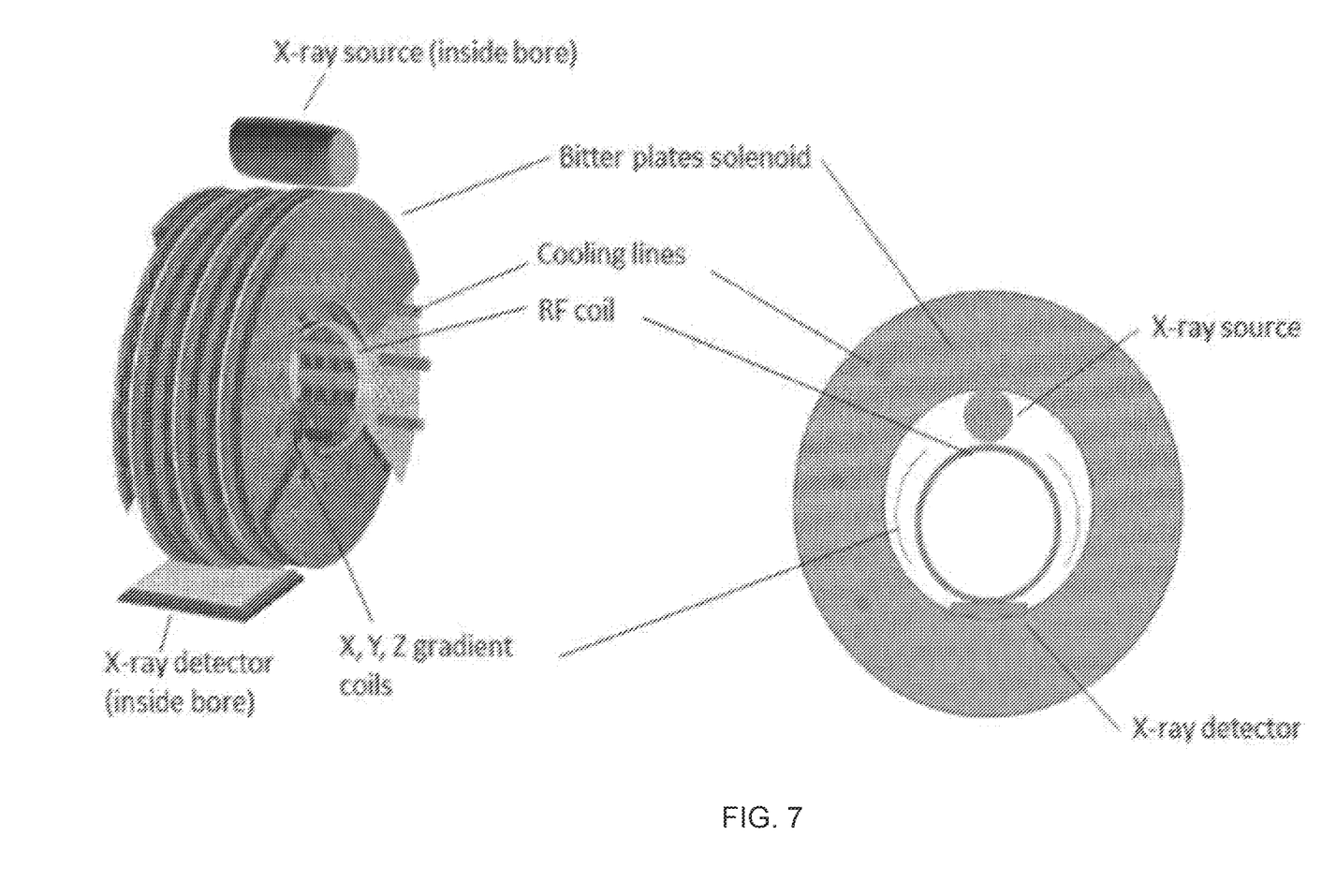
FIG. 7 shows a schematic view of an MRX system according to an embodiment of the subject invention.

FIG. 7 shows a schematic view of a MRX system according to an embodiment of the subject invention. Though the X-ray source and X-ray detector are depicted on the left-hand portion of FIG. 7 as being outside the bore or gantry, this is for visual simplification only; these elements would actually be inside, as depicted on the right-hand portion of FIG. 7. Referring to FIG. 7, the system can include one or more bitter plates solenoids, along with the required cooling lines, as the means for generating the magnetic field. FIG. 7 depicts the gradient coils and RF coil of the system. The subject to be imaged can be placed within the magnetic field inside the bore of the solenoid, between the X-ray source and the X-ray detector.

Figure 8:
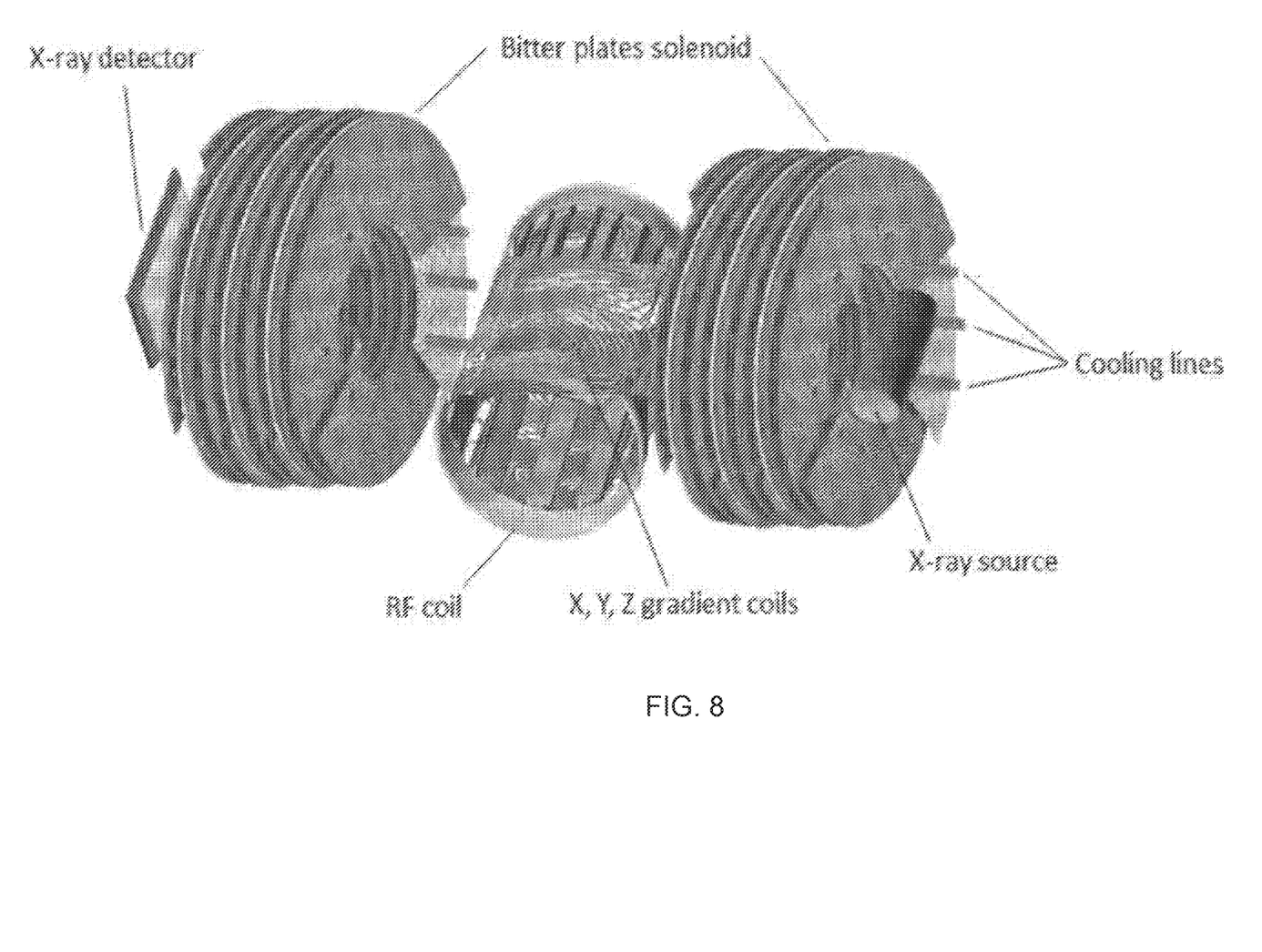
FIG. 8 shows a schematic view of an MRX system according to an embodiment of the subject invention.

FIG. 8 shows a schematic view of a MRX system according to an embodiment of the subject invention. Referring to FIG. 8, the subject to be imaged can be placed inside the RF coil within the magnetic field between two solenoids. The X-ray source and the X-ray detector can positioned outside the RF coil on the opposite side of the respective solenoid from the RF coil. Alternatively, one or both of the X-ray source and the X-ray detector can be placed within the respective solenoid bore. FIG. 8 depicts the gradient coils and RF coil of the system.

Spiral MRX systems according to embodiments of the subject invention enable the simultaneous acquisition of X-ray (e.g., CT X-ray) and MRI data for hybrid tomographic imaging of a subject (e.g., a head, spine, and/or extremities of a human patient). A system with permanent magnets as the means for generating a magnetic field can achieve fields between 0.1 T and 0.2 T while keeping weight low enough for portability. For extremity imaging, specifically in knees, low-field MRI at 0.2 T can be clinically viable for diagnosing ligament and meniscus damage. These field strengths can achieve satisfactory image quality for other applications, such as head and spine imaging, though higher fields can yield higher resolution. Field strengths of, for example, up to 0.35 T, are achievable with permanent magnets that keep a compact profile, though increased weight can compromise ease of transportation. The fringe magnetic field at the location of the X-ray source can be greatly reduced by a steel flux return.

To increase the magnetic field homogeneity, decrease the peripheral field, and optimize the system compactness, high-temperature superconducting wires can be used. Superconducting wires that have been developed so far are lightweight and thin compared to existing copper conducting wires, and can accommodate a cryostat line inside the cable (van der Laan et al., "Compact GdBa 2 Cu 3 O 7-5 coated conductor cables for electric power transmission and magnet applications," Supercond. Sci. Technol., vol. 24, no. 4, p. 042001 (1-6), 2011; which is hereby incorporated herein by reference in its entirety; and Jang et al, "Superconducting cable," U.S. Patent Application Publication No. 2013/0165324, 2013; which is hereby incorporated herein by reference in its entirety). They have a high current-carrying capacity that could allow higher field strengths to be achieved than those from permanent magnets. A major challenge with superconductors remains the necessity for cooling (e.g., cryogenic cooling).

A similar alternative design is superconducting optical fibers instead of permanent magnets. Homa et al. ("Superconducting fiber," Appl. Phys. Lett., vol. 103, no. 82601, pp. 1-4, 2013; "Superconducting tin core fiber," Appl. Phys. A Mater. Sci. Process., vol. 118, no. 1, pp. 23-26, 2014; "Efficient cooling of superconducting fiber core via holey cladding," Cryogenics, vol. 61, pp. 25-30, 2014; all three of which are hereby incorporated herein by reference in their entireties) have tested fibers with lead and tin cores for superconductivity in a liquid helium bath at 4 K. Fibers injected with liquid helium can exhibit superconductivity for an extended period of time while they warm to room temperature. In the context of MRX, superconducting fibers could be wound into coils and used to create a homogeneous local magnetic field on the order of 0.2 T. The conditions for superconductivity are much simpler to achieve than large-scale cryogenic superconducting magnets.

MRX systems and methods of embodiments of the subject invention have many important applications. For extremity trauma, MRX can deliver both bone information from CT and soft tissue information from MR. This can help assess bony trauma from X-rays while determining the presence, extent, and severity of associated soft tissue problems involving muscles, joints, tendons, and blood vessels from MRI. Rapid detection of devastating vascular injuries can help in prompt triage and management decisions with limb- and life-saving implications. For example, in non-hospital settings (e.g., military and natural or manmade disaster settings), the presence of extensive soft tissue injury or vascular complications can warrant expedited transport or triage for rapid treatment. Simultaneous and rapid spiral MRX enables synergistic CT and MR with complementary information, perfect co-registration, and potentially multi-variable pixel information.

Spiral MRX in battlefield and sites of major disasters can be very advantageous in on-site, out-of-hospital settings for rapid triage and management of suspected or known spinal injuries. Current workup is only possible in elaborate and expensive non-portable healthcare settings with plain film radiography and CT to delineate bony injuries and MR for detection of injuries to the spinal cord and nerves, as well as the vital supporting soft tissues such as ligaments, muscles, and joints. Portable MRX can rapidly provide on-site information not obtainable with either one when used separately. In case of bullet wounds and other metal shrapnel, additional precautions can be used to ensure that the magnetic field does not significantly move the object within the body.

An MRX system can alternatively work in the radiographic imaging mode, where two-dimensional radiography can provide information on bony alignment and fragments, while MRI adds the missing third dimension to radiographic information and provides information on injuries to spinal cord, nerves, and ligaments. Likewise, head injuries are a major cause for disability and deaths, which can also be rapidly assessed with spiral MRX in non-hospital settings. While CT is the modality of choice for injuries to the bony cranium and for acute intracranial hemorrhage, MR outperforms every other known imaging modality for evaluation of injury to brain parenchyma. Combining modalities with MRX provides a one-stop, accurate, and rapid categorization of the presence and severity of head trauma and can potentially mitigate some devastating outcomes of these injuries.

Beyond trauma, MRX can provide better information on the presence and severity of ischemic strokes and possibly other causes of acute neurological symptoms from insults to the brain parenchyma, as compared to rather limited information now generated with CT or with a stationary time-consuming MR examination in a healthcare setting. Further, in post-stent or angioplasty events, MRX can even provide information on luminal patency and recovered or non-recovered myocardium.

Currently, coronary catheterization is the very important for luminal stenosis in ischemic heart disease. CT is useful to triage patients who can be safely discharged versus patients who need invasive coronary catheterization (ICA) with a C-arm x-ray assembly. MR is typically used for anything myocardial (congenital, inflammatory, neoplastic conditions), and most importantly for determining cardiac function and extent of damage as well as chances of salvaging myocardial function following revascularization (coronary artery bypass grafting or stent placement in coronary arteries). MRX may also minimize or obviate the need for high radiation dose CT because the structural information can be acquired at extremely low levels of radiation for evaluation of lungs and bones, and soft tissue information typically requiring higher dose CT can instead be filled-in with the superior contrast resolution of MR.

The combination of spiral CT and MRI enables excellent spatial resolution and low-contrast resolution to be provided in a single scan. Permanent magnets can be used to decrease cost and weight, and a lightweight, low-power x-ray source can be used to minimize radiation dose. A flat panel detector can be used in a compact gantry. The spiral acquisition protocol can allow for good coverage along the Z-direction for both modalities. In addition to its widespread potential in hospital settings, the MRX system has can also be used for imaging at, for example, disaster sites, battle fields, and under-developed regions.

The methods and processes described herein can be embodied as code and/or data. The software code and data described herein can be stored on one or more machine-readable media (e.g., computer-readable media), which may include any device or medium that can store code and/or data for use by a computer system. When a computer system and/or processor reads and executes the code and/or data stored on a computer-readable medium, the computer system and/or processor performs the methods and processes embodied as data structures and code stores within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that is capable of storing computer-readable information/data. Computer-readable media should not be construed or interpreted to include any propagating signals. A computer-readable medium of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

The subject invention includes, but is not limited to, the following exemplified embodiments.

Embodiment 1. A system for performing simultaneous X-ray imaging and magnetic resonance imaging (MRI), the system comprising:
an X-ray source;
an X-ray detector for detecting X-rays from the X-ray source;
a radio frequency (RF) coil;
at least one gradient coil; and
means for generating a magnetic field for MR imaging,
wherein the system is configured such that, during imaging of a subject:
the X-ray source and X-ray detector are simultaneously rotated around the subject; and
the means for generating a magnetic field is rotated around the subject.

Embodiment 2. The system according to embodiment 1, wherein the system is configured such that, during imaging of a subject, the X-ray source, the X-ray detector, and the means for generating a magnetic field are also all translated longitudinally (e.g., along an axis of the circular or spiral path of the rotation of these elements) along a region of interest of the subject.

Embodiment 3. The system according to any of embodiments 1-2, wherein the means for generating a magnetic field comprises a plurality of permanent magnets.

Embodiment 4. The system according to any of embodiments 1-3, wherein the means for generating a magnetic field comprises a plurality of permanent magnets arranged in a Halbach configuration.

Embodiment 5. The system according to any of embodiments 1-4, wherein the means for generating a magnetic field comprises a plurality of permanent magnets arranged in a plurality of magnet rings.

Embodiment 6. The system according to embodiment 5, comprising two magnet rings disposed such that their radii are parallel (or substantially parallel) to each other.

Embodiment 7. The system according to any of embodiments 5-6, wherein each magnet ring comprises a plurality of magnet blocks.

Embodiment 8. The system according to embodiment 7, wherein each magnet ring comprises eight magnet blocks.

Embodiment 9. The system according to any of embodiments 7-8, wherein each magnet ring is configured such that each of its magnet blocks has corresponding polarity to that in the same position on the other magnet ring(s).

Embodiment 10. The system according to any of embodiments 6-9, wherein the two magnet rings disposed such that their radii are parallel (or substantially parallel) to each other comprise a first magnet ring and a second magnet ring, and wherein the means for generating a magnetic field comprises a partial third magnet ring disposed between (in an axial direction perpendicular to the radii of the first and second magnet rings) the first and second magnet rings, the partial third magnet ring having less magnet blocks than either of the first magnet ring and the second magnet ring.

Embodiment 11. The system according to any of embodiments 1-4, wherein the means for generating a magnetic field comprises a plurality of permanent magnet bars arranged in magnet bar arrangement.

Embodiment 12. The system according to any of embodiments 1-4, wherein the means for generating a magnetic field comprises a plurality of resistive magnet coils.

Embodiment 13. The system according to any of embodiments 1-4 and 12, wherein the means for generating a magnetic field comprises a plurality of solenoids.

Embodiment 14. The system according embodiment 13, wherein each solenoid is a Bitter plates solenoid.

Embodiment 15. The system according to any of embodiments 13-14, wherein the X-ray source and the X-ray detector are both disposed in a bore of the solenoids.

Embodiment 16. The system according to any of embodiments 14-15, wherein the system is configured such that the subject to be imaged is placed inside a bore of the solenoids.

Embodiment 17. The system according to any of embodiments 13-15, wherein the RE coil is disposed between two solenoids, and wherein the system is configured such that the subject to be imaged is placed inside the RE coil.

Embodiment 18. The system according to any of embodiments 13-14 and 17, wherein the X-ray source and the X-ray detector are both disposed outside the RE coil and outside bores of the solenoids.

Embodiment 19. The system according to any of embodiments 13-14 and 17, wherein the X-ray source is disposed outside the RE coil and in a bore of a first solenoid of the plurality of solenoids.

Embodiment 20. The system according to any of embodiments 13-14, 17, and 18, wherein the X-ray detector is disposed outside the RE coil and in a bore of a second solenoid of the plurality of solenoids.

Embodiment 21. The system according to any of embodiments 1-4, wherein the means for generating a magnetic field comprises a plurality of superconducting magnets.

Embodiment 22. The system according to any of embodiments 1-21, wherein the means for generating a magnetic field generates a magnetic field with a maximum strength of 0.50 T or less.

Embodiment 23. The system according to any of embodiments 1-21, wherein the means for generating a magnetic field generates a magnetic field with a maximum strength of 0.35 T or less.

Embodiment 24. The system according to any of embodiments 1-21, wherein the means for generating a magnetic field generates a magnetic field with a maximum strength of 0.34 T or less.

Embodiment 25. The system according to any of embodiments 1-21, wherein the means for generating a magnetic field generates a magnetic field with a maximum strength of 0.30 T or less.

Embodiment 26. The system according to any of embodiments 1-21, wherein the means for generating a magnetic field generates a magnetic field with a maximum strength of 0.25 T or less.

Embodiment 27. The system according to any of embodiments 1-21, wherein the means for generating a magnetic field generates a magnetic field with a maximum strength of 0.20 T or less.

Embodiment 28. The system according to any of embodiments 1-27, further comprising a machine (e.g., a computer) for reconstructing the image(s) of the subject to be imaged.

Embodiment 29. The system according to embodiment 28, wherein the machine has one or more machine readable media (e.g., one or more computer readable media) having machine-executable (e.g., computer-executable) instructions (stored thereon) for performing a method for reconstructing the image(s) of the subject to be imaged.

Embodiment 30. The system according to embodiment 29, wherein the method for reconstructing the image(s) of the subject to be imaged comprises:

i) reconstructing X-ray (e.g., X-ray computed tomography (CT)) and MRI images using the simultaneous algebraic reconstruction technique with total variation (SART-TV) to obtain convex optimization equations;

ii) combining structural coupling and compressive sensing techniques, in which each sub-image is represented by paired local X-ray (e.g. X-ray CT)-MRI structures to obtain convex optimization equations; and iii) solving the convex optimization equations from steps i) and ii).

Embodiment 31. The system according to embodiment 30, wherein solving the convex optimization equations from steps i) and ii) comprises solving the convex optimization equations using a split-Bregman framework.

Embodiment 32. The system according to any of embodiments 30-31, wherein step i) comprises using the following equations:

$$\min_{u_{CT}} \|u_{CT}\|_{TV}, \text{s.t.} \ Mu_{CT} = f, \text{and}$$

$$\min_{u_{MRI}} \|u_{MRI}\|_{TV}, \text{s.t.} \ RFu_{MRI} = g,$$

where $u_{CT}$ and $u_{MRI}$ are respectively X-ray (e.g., X-ray CT) and MR images to be reconstructed, M is a system matrix in X-ray (e.g., X-ray CT) imaging, F denotes the Fourier transform, R is a sampling mask in the k-space, f and g are X-ray (e.g., X-ray CT) and MRI measurements, respectively, and $\|\cdot\|_{TV}$ denotes the TV transformation.

Embodiment 33. The system according to embodiment 32, wherein step i) comprises using an artificial neural network to guide both X-ray (e.g., X-ray CT) and MRI reconstructions using the equations presented in embodiment 32.

Embodiment 34. The system according to any of embodiments 30-33, wherein step ii) comprises using the following equations:

$$\min_{u_{CT}}(1-\alpha)\|u_{CT}\|_{TV} + \alpha\|u_{CT} - u_{CT}^{est}\|_{TV}, \text{s.t.} \ Mu_{CT} = f, \text{and}$$

$$\min_{u_{MRI}}(1-\alpha)\|u_{MRI}\|_{TV} + \alpha\|u_{MRI} - u_{MRI}^{est}\|_{TV}, \text{s.t.} \ RFu_{MRI} = g,$$

where $u_{CT}$ and $u_{MRI}$ are respectively X-ray (e.g., X-ray CT) and MR images to be reconstructed, M is a system matrix in X-ray (e.g., X-ray CT) imaging, F denotes the Fourier transform, R is a sampling mask in the k-space, f and g are X-ray (e.g., X-ray CT) and MRI measurements, respectively, $\|\cdot\|_{TV}$ denotes the TV transformation, $u_{CT}^{est}$ and $u_{MRI}^{est}$, are estimated images using the X-ray (e.g., X-ray CT)-MRI artificial neural network according to the corresponding X-ray (e.g., X-ray CT) and MRI images, respectively, a balances contributions from total variation and image similarity, respectively.

Embodiment 35. The system according to embodiment 34, wherein step ii) comprises using an artificial neural network to guide both X-ray (e.g., X-ray CT) and MRI reconstructions using the equations presented in embodiment 34.

Embodiment 36. The system according to any of embodiments 1-35, wherein the X-ray detector is a flat detector array.

Embodiment 37. The system according to any of embodiments 1-36, wherein the at least one gradient coil comprises an X gradient coil, a Y gradient coil, and a Z gradient coil.

Embodiment 38. The system according to any of embodiments 1-37, wherein the means for generating a magnetic field is disposed such that no portion of it is interposed between the X-ray source and the X-ray detector.

Embodiment 39. A method for performing simultaneous X-ray imaging and magnetic resonance imaging (MRI), the method comprising: providing a subject to be imaged; and using the system according to any of embodiments of 1-38 to perform simultaneous X-ray imaging and MRI on the subject.

A greater understanding of the present invention and of its many advantages may be had from the following examples, given by way of illustration. The following examples are illustrative of some of the methods, applications, embodiments, and variants of the present invention. They are, of course, not to be considered as limiting the invention. Numerous changes and modifications can be made with respect to the invention.

Example 1

A system as shown in FIG. 1A was simulated (though the gradient coils and RF coil needed for MRI are not shown in FIG. 1A, these were present in the simulation). Each magnet ring included eight permanent magnets, as shown in FIG. 1B. Simulations to assess magnetic field strength were performed using FARADAY (Integrated Engineering Software, Winnipeg, Manitoba), which is a 3D solver of Maxwell's equations that employs finite element methods.

The ever-present field of permanent magnets eliminated the need for a high current source, but weight is an issue for portability, as the rare-earth metals are dense. The material of each permanent magnet was NdFeB 45 MGOe Sintered, which is an alloy of neodymium, iron, and boron, and has a density of 7.5 g/cm3. FIG. 1A illustrates two rings of magnets arranged in a simplified Halbach configuration, with each ring containing eight blocks with the magnetization directions as shown in FIG. 1B. Each ring had an inner diameter of 30 cm, an outer diameter of 60 cm, and a thickness of 5 cm, and the rings were separated by 20 cm. The total weight of all 16 magnet blocks in both rings was 158 kg. The X-ray hardware was positioned above and below the patient and can be rotated in a full circle while the patient table is translated during spiral CT and MR scanning. A magnetic field on the order of 0.11 T was present in a 10 cm cubic imaging region between the rings, as shown in the front view in FIG. 1C. FIG. 1D displays a side view of the magnetic field in the imaging region. The field can be increased by increasing the volume of the magnets, but this also increases weight, which would hinder the portability of the system. The fringe magnetic field was plotted as shown in FIG. 1E. At a distance of 35 cm above the center of the Bo field where the X-ray source is located, the field strength was about 0.0064 T, or about 6% of Bo. With steel flux return blocks added at the bottom of the magnet rings, the fringe field strength at the position of the X-ray source was reduced by nearly half, to 0.0034 T, as depicted in FIG. 1F.

As an extension, a partial third ring was added between the other two with only the four side magnet blocks present to preserve space for the X-ray components, as shown in FIG. 1G. This addition increased the field strength to about 0.16 T at the center of the imaging region, as indicated in FIG. 1H, though the total magnet weight increased to 198 kg. The design can be further optimized to balance field strength and weight.

The field strength deviations were about 5% in the imaging region of interest. The MRI reconstruction algorithm can handle slight inhomogeneity in the Bo field with special pulse sequences and dedicated techniques. However, a homogeneous field in the imaging region of interest makes reconstruction easier. A potential way to improve could be to modify magnetic surfaces and add shimming coils. Also, field homogeneity can be improved via dedicated shaping of the magnets. Specifically, the boot surfaces, based on parabolic or hyperbolic functions, modify the magnetic field distribution to maintain a greater homogeneity over a region of interest for imaging.

Example 2

A system as shown in FIG. 2A was simulated (though the gradient coils and RF coil needed for MRI are not shown in FIG. 2A, these were present in the simulation). The bar magnet arrangement was as shown in FIG. 2B. Simulations to assess magnetic field strength were performed using FARADAY.

Figures 2D, 2E:
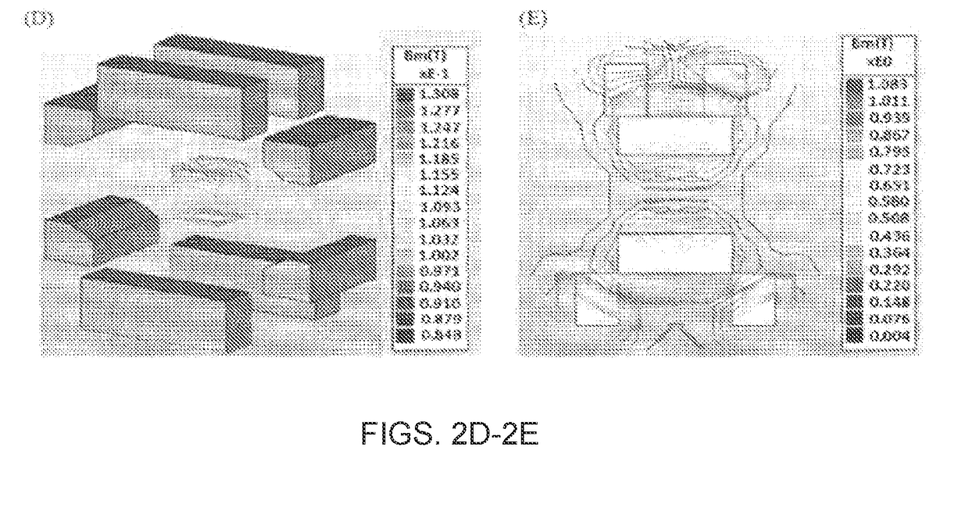
FIG. 2D shows an isometric view of the magnetic field produced by a bar magnet arrangement that can be used with an MRX system according to an embodiment of the subject invention.
FIG. 2E shows a side view of the fringe magnetic field around the gantry produced by a bar magnet arrangement that can be used with an MRX system according to an embodiment of the subject invention.

The magnet bars above and below the patient were 30 cm wide along the largest dimension and each weighed approximately 17 kg. The two top magnets were separated by 10 cm to allow room for the X-ray window of the tube. The bottom two magnets were separated by 20 cm to accommodate the flat panel detector. Additionally, there were two pairs of magnet bars flanking either side of the patient measuring 20 cm in length along their largest dimension. Each of these blocks weighed a little over 10 kg, which brought the total weight of the configuration to approximately 109 kg. The magnet polarities of these bars were as shown in FIG. 2B. A magnetic field on the order of 0.11 T with a natural gradient was present in a 10 cm cube imaging region at the center of the bars, as shown in FIG. 2C. FIG. 2D displays an isometric view of the magnetic field in the imaging region. The fringe magnetic field around the system is plotted in FIG. 2E. At a distance of 30 cm above the center of the Bo field where the X-ray source was located, the field strength was about 0.035 T, which is relatively high compared with Bo. A steel return did not have a significant effect on the fringe field in this configuration.

Example 3

Figures 3A, 3B:
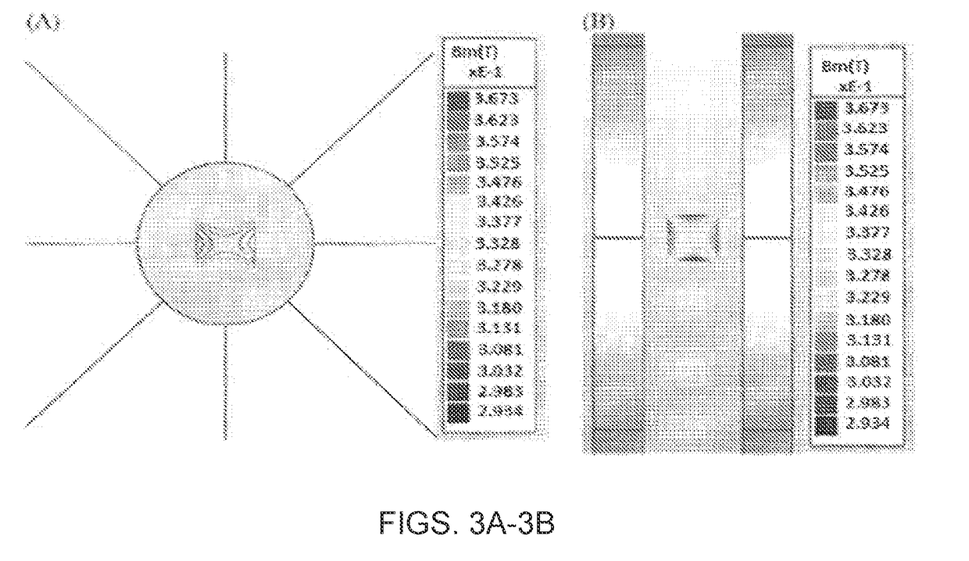
FIG. 3A shows a view of the magnetic field produced by a magnet ring that can be used with an MRX system according to an embodiment of the subject invention.
FIG. 3B shows a side view of the magnetic field produced by a magnet ring that can be used with an MRX system according to an embodiment of the subject invention.

While the designs shown in FIGS. 1 and 2 present compact, lightweight magnet designs that are ideal for a portable spiral MRX system, the field strength may be low and may not produce the desired extremely high-resolution images in certain applications. The field can be increased by expanding the outer diameter and thickness of the magnet rings. Of course, weight will also increase, which hinders the mobility of the scanner. FIG. 3 offers an additional two-ring design in the same configuration as FIGS. 1A-1D, but with larger ring thicknesses and diameters. Simulations to assess magnetic field strength on this system were performed using FARADAY.

FIGS. 3A and 3B show front and side views, respectively, of the magnetic field, which had a strength of about 0.34 T in a 10 cm cubic region between the rings. The rings each had an inner bore diameter of 30 cm, an outer diameter of 120 cm, and a thickness of 10 cm, and were separated by 20 cm. The total weight of all 16 magnet blocks in both rings was 1,589 kg. For comparison, a commercially available MRI scanner that utilizes superconducting magnets typically weighs at least 7,000 kg. The specifications of the magnet designs presented in the examples are summarized in Table1. Though Table 1 refers to specific figure numbers, those are only for ease with respect to the examples; this does not mean that the system shown in these figures must have the dimensions, weight, magnetic field strength and other characteristics shown in Table 1 and discussed in the examples.

TABLE 1

Comparison of the presented magnet designs

| Design | Weight | Central $B_0$ Field Strength | Homogeneity Deviation Within ROI (approx.) |
|---|---|---|---|
| FIG. 1(A-E) | 158 kg | 0.11 T | 5% |
| FIG. 1(G-H) | 198 kg | 0.16 T | 10% |
| FIG. 2 | 109 kg | 0.11 T | 20% |
| FIG. 3 | 1,589 kg | 0.34 T | 6% |

Example 4

Figures 5A, 5B, 5C, 5D, 5E, 5F:
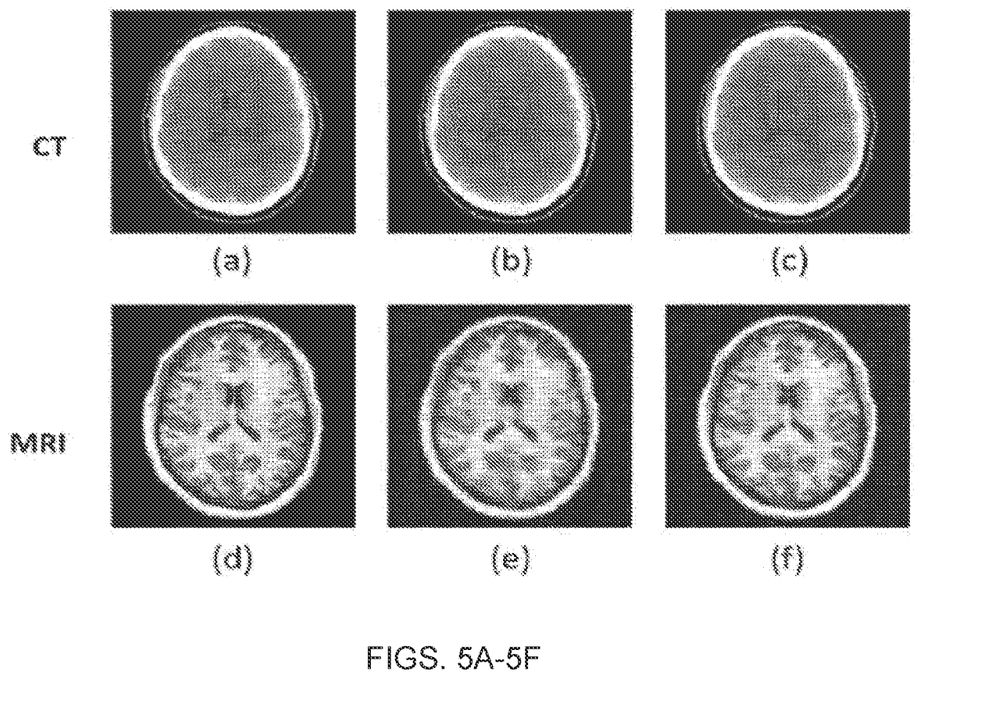
FIG. 5A shows a CT image from the visible human project (VHP).
FIG. 5B shows a reconstructed CT version of the image of FIG. 5A.
FIG. 5C shows a reconstructed CT version, including use of MRI data, of the image of FIG. 5A.
FIG. 5D shows an MRI image from the VHP.
FIG. 5E shows a reconstructed MRI version of the image of FIG. 5D.
FIG. 5F shows a reconstructed MRI version, including use of CT data, of the image of FIG. 5D.

Numerical simulations were performed to evaluate the learning-based CT-MRI reconstruction method discussed herein. CT and MRI datasets were derived from the Visible Human Project (VHP). An identical human head model was sequentially scanned by CT and MRI scanners. The acquisition process is illustrated in FIGS. 4A-4C. The CT and MR images were pre-processed for spatial registration and voxel normalization. The numerical phantom used for CT is shown in FIG. 5A, and the numerical phantom used for MR is shown in FIG. 5D; both had an image size of 212×212 pixels. In the CT-MRI artificial neural network, well-registered CT and MRI images were taken as inputs.

In CT imaging, 30 projections were collected around the phantom shown in FIG. 5A. Due to the concern of X-ray radiation during CT imaging, an aim was to minimize the ionizing radiation level needed while maintaining a suitable image quality. Hence, 30 projections were used in the simulation, which is consistent with the number of views used for sparse-view CT. In MRI scanning, low-field measurement data were obtained in 30 rotation steps for the phantom of FIG. 5D. The Bo field was inhomogeneous and modeled after a rotating Halbach gantry.

The average field strength was simulated at 0.08 T to demonstrate the minimum capability of the system. The inhomogeneous Bo field was treated as a superposition of an ideal homogeneous field and an additional gradient field, and as the Bo field was rotated, independent data were collected for image reconstruction. The initial CT and MRI reconstructions using the SART-TV method are displayed in FIGS. 5B and 5E, respectively. In the joint image reconstruction of the MRX system, a unified scheme was applied in which the CT image and MR image were connected by coupling their structures to guide each reconstruction. The reconstructed images using the unified CT-MRI scheme are shown in FIGS. 5C and 5F, respectively.

Figure 6A:
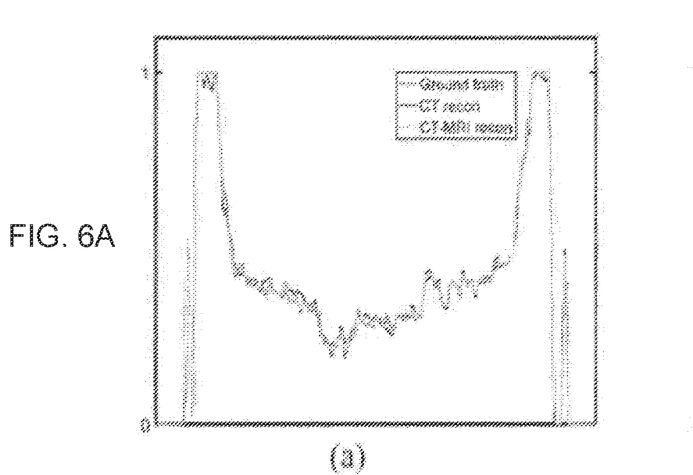
FIG. 6A shows a plot of line profiles of CT and unified CT-MRI reconstructions.
Figure 6B:
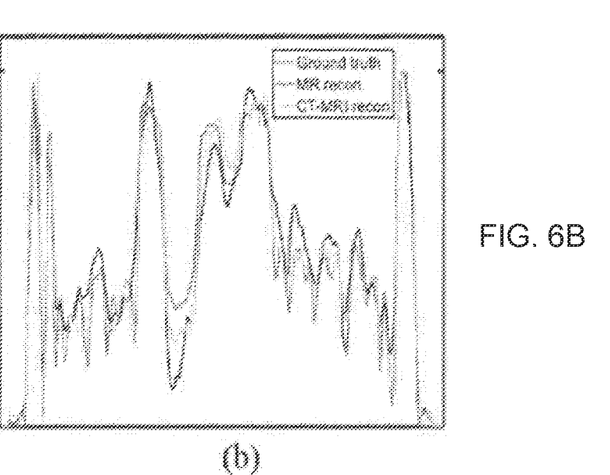
FIG. 6B shows a plot of line profiles of MR and unified CT-MRI reconstructions.
Figure 6C:
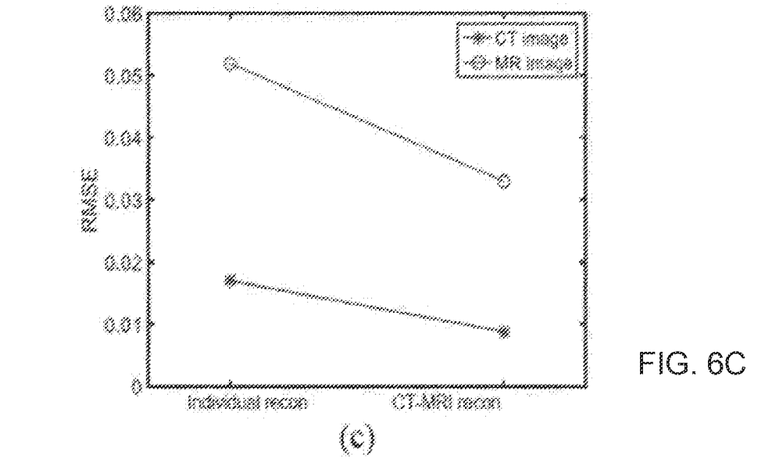
FIG. 6C shows a plot of the root-mean-square error (RMSE) for the CT image (lower, darker line, with the "X" data points) and the MR image (upper, lighter line, with the "O" data points).

Quantitative comparison of the reconstructed images with the ground truth is presented in FIGS. 6A-6C, in which vertical line profiles of each resultant image from FIG. 5 are plotted. FIG. 6A shows a plot of line profiles of CT and unified CT-MRI reconstructions, FIG. 6B shows a plot of line profiles of MR and unified CT-MRI reconstructions, and FIG. 6C shows a plot of the root-mean-square error (RMSE) for the CT image (lower, darker line, with the "X" data points) and the MR image (upper, lighter line, with the "O" data points). The RMSE was employed to measure the reconstruction accuracy. Referring to FIG. 6C, the unified CT-MRI reconstruction technique results in less error than individual CT and MRI reconstructions via SART-TV.

When the term "about" is used herein, in conjunction with a numerical value, it is understood that the value can be in a range of 95% of the value to 105% of the value, i.e. the value can be +/−5% of the stated value. For example, "about 1 kg" means from 0.95 kg to 1.05 kg.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein (including those in the "References" section) are incorporated by reference in their entirety, including all figures and tables, to the extent they are not inconsistent with the explicit teachings of this specification.

REFERENCES

1. G. Wang, J. Zhang, H. Gao, V. Weir, H. Yu, W. Cong, X. Xu, H. Shen, J. Bennett, M. Furth, Y. Wang, and M. Vannier, "Towards omni-tomography-grand fusion of multiple modalities for simultaneous interior tomography," PLoS One, vol. 7, no. 6, 2012.
2. L. Gjesteby, M. Getzin, and G. Wang, "Low-field designs for interior MRI and CT coupling," in 2015 Northeast Biomedical Engineering Conference (NEBEC), 2015, pp. 1-2.
3. G. Wang, M. Kalra, V. Murugan, Y. Xi, L. Gjesteby, M. Getzin, Q. Yang, W. Cong, M. Vannier, "Vision 20/20: Simultaneous CT-MRI—Next chapter of multimodality imaging," Med. Phys., vol. 42, no. 10, pp. 5879-5889, 2015.
4. V. R. Yelleswarapu, F. Liu, W. Cong, and G. Wang, "Top-Level System Designs for Hybrid Low-Field MRI-CT with Potential of Pulmonary Imaging," Sens. Imaging, vol. 15, no. 1, p. 98, October 2014.
5. Z. Wen, R. Fahrig, S. Conolly, and N. J. Pelc, "Investigation of electron trajectories of an x-ray tube in magnetic fields of MR scanners," Med. Phys., vol. 34, no. 6, pp. 2048-2058, 2007.
6. L. L. Tsai, R. W. Mair, M. S. Rosen, S. Patz, and R. L. Walsworth, "An open-access, very-low-field MRI system for posture-dependent 3 He human lung imaging," J. Magn. Reson., vol. 193, no. 2, pp. 274-285, 2008.
7. C. Z. Cooley, J. P. Stockmann, B. D. Armstrong, M. Sarracanie, M. H. Lev, M. S. Rosen, and L. L. Wald, "Two-dimensional imaging in a lightweight portable MRI scanner without gradient coils," Magn. Reson. Med., vol. 73, pp. 872-883, 2015.
8. H. Yu and G. Wang, "Compressed sensing based interior tomography," Phys. Med. Biol., vol. 54, no. 9, p. 2791, 2009.
9. G. Wang and H. Yu, "The meaning of interior tomography," Phys. Med. Biol., vol. 58, no. 16, p. R161, 2013.
10. R. Fahrig, K. Butts, J. A. Rowlands, R. Saunders, J. Stanton, G. M. Stevens, B. L. Daniel, Z. Wen, D. L. Ergun, and N. J. Pelc, "A truly hybrid interventional MR/X-ray system: Feasibility demonstration," J. Magn. Reson. Imaging, vol. 13, no. 2, pp. 294-300, 2001.
11. G. Wang and M. W. Vannier, "Low-contrast resolution in volumetric x-ray CT-analytical comparison between conventional and spiral CT," Med. Phys., vol. 24, no. 3, pp. 373-376, 1997.
12. B. K. Halbach, L. Berkeley, U. C. Berkeley, and B. Ca, "Physical and Optical Properties of Rare Earth Cobalt Magnets Magnets for Particle Optics," Nucl. Instruments Methods, pp. 1-10, 1981.
13. R. Bjerk, C. R. H. Bahl, a. Smith, and N. Pryds, "Optimization and improvement of Halbach cylinder design," J. Appl. Phys., vol. 104, no. 1, pp. 1-9, 2008.
14. P. Suetens, Fundamentals of medical imaging. Cambridge University Press, 2009.
15. P. Blumler, "Proposal for a permanent magnet system with a constant gradient mechanically adjustable in direction and strength," Concepts Magn. Reson. Part B Magn. Reson. Eng., 2016.
16. M. D. Bird, I. R. Dixon, and J. Toth, "Design of the next generation of Florida-bitter magnets at the NHMFL," IEEE Trans. Appl. Supercond., vol. 14, no. 2, pp. 1253-1256, 2004.

17. M. Ristic, Y. Gryska, J. V. M. McGinley, and V. Yufit, "Supercapacitor Energy Storage for Magnetic Resonance Imaging Systems," Ind. Electron. IEEE Trans., vol. 61, no. 8, pp. 4255-4264, 2014.
18. C. Liu, Z. Yu, D. Neff, A. Zhamu, and B. Z. Jang, "Graphene-based supercapacitor with an ultrahigh energy density," Nano Lett., vol. 10, no. 12, pp. 4863-4868, 2010.
19. T. Lin, I.-W. Chen, F. Liu, C. Yang, H. Bi, F. Xu, and F. Huang, "Nitrogen-doped mesoporous carbon of extraordinary capacitance for electrochemical energy storage," Science., vol. 350, no. 6267, pp. 1508-1513, December 2015.
20. Y. Xi, J. Zhao, J. Bennett, M. Stacy, A. Sinusas, and G. Wang, "Simultaneous CT-MRI Reconstruction for Constrained Imaging Geometries using Structural Coupling and Compressive Sensing," IEEE Trans. Biomed. Eng., vol. 63, no. 6, pp. 1301-1309, 2016.
21. Y. Xi, Y. Chen, R. Tang, J. Sun, and J. Zhao, "United iterative reconstruction for spectral computed tomography," Med. Imaging, IEEE Trans., vol. 34, no. 3, pp. 769-778, 2015.
22. B. Vandeghinste, B. Goossens, J. De Beenhouwer, A. Pizurica, W. Philips, S. Vandenberghe, and S. Staelens, "Split-Bregman-based sparse-view CT reconstruction," in 1 Ith International meeting on Fully Three-Dimensional Image Reconstruction in Radiology and Nuclear Medicine (Fully 3D 11), 2011, pp. 431-434.
23. B. Kladny, K. Gluckert, B. Swoboda, W. Beyer, and G. Weseloh, "Comparison of low-field (0.2 Tesla) and high-field (1.5 Tesla) magnetic resonance imaging of the knee joint," Arch. Orthop. Trauma Surg., vol. 114, no. 5, pp. 281-286, 1995.
24. W. Mao and G. Wang, "TU—H-BRA-05: A System Design for Integration of An Interior MRI and a Linear Accelerator," Med. Phys., vol. 43, no. 6, p. 3769, 2016.
25. G. Krainz, "Quench Protection and Powering in a String of Superconducting Magnets for the Large Hadron Collider," CERN, 1997.
26. R. Soika, N. Diaczenko, T. Elliott, W. Henchel, E. Hill, G. Liang, P. McIntyre, L. Motowidlo, and M. Yavuz, "Fabrication and prototype testing of a strain-tolerant Bi-2212 cable," IEEE Trans. Appl. Supercond., vol. 11, no. 1, pp. 2142-2145, 2001.
27. A. P. Drozdov, M. I. Eremets, I. A. Troyan, V. Ksenofontov, and S. I. Shylin, "Conventional superconductivity at 203 kelvin at high pressures in the sulfur hydride system," Nature, vol. 525, no. 7567, pp. 73-76, September 2015.
28. D. C. van der Laan, X. F. Lu, and L. F. Goodrich, "Compact GdBa 2 Cu 3 O 7-5 coated conductor cables for electric power transmission and magnet applications," Supercond. Sci. Technol., vol. 24, no. 4, p. 042001 (1-6), 2011.
29. H. M. Jang, S. K. Lee, Y. W. Kim, and C. H. Ryu, "Superconducting cable," US20130165324, 2013.
30. D. Homa, Y. Liang, G. Pickrell, D. Homa, Y. Liang, and G. Pickrell, "Superconducting fiber," Appl. Phys. Lett., vol. 103, no. 82601, pp. 1-4, 2013.
31. D. Homa, Y. Liang, C. Hill, G. Kaur, and G. Pickrell, "Superconducting tin core fiber," Appl. Phys. A Mater. Sci. Process., vol. 118, no. 1, pp. 23-26, 2014.
32. D. Homa, G. Kaur, G. Pickrell, and Y. Liang, "Efficient cooling of superconducting fiber core via holey cladding," Cryogenics, vol. 61, pp. 25-30, 2014.
33. E. Martinez-del-Campo, L. Rangel-Castilla, H. Soriano-Baron, and N. Theodore, "Magnetic resonance imaging in lumbar gunshot wounds: an absolute contraindication?," Neurosurg. Focus, vol. 37, no. 1, p. E13, 2014.
34. Wang et al., International Patent Application Publication No. WO2016/106348.
35. Wang et al., U.S. Patent Application Publication No. 2015/0157286.
36. Wang et al., U.S. Patent Application Publication No. 2015/0170361.
37. Wang et al., U.S. Patent Application Publication No. 2015/0193927.
38. Wang et al., International Patent Application Publication No. WO2015/164405.
39. Wang et al., U.S. Patent Application Publication No. 2016/0113602.
40. Wang et al., U.S. Patent Application Publication No. 2016/0135769.
41. Wang et al., U.S. Patent Application Publication No. 2016/0166852.
42. Wang et al., International Patent Application Publication No. WO2016/106348.
43. Wang et al., International Patent Application No. PCT/US2016/014769.
44. Wang et al., International Patent Application No. PCT/US2016/023460.
45. Wang et al., International Patent Application No. PCT/US2016/036057.
46. Wang et al., International Patent Application No. PCT/US2016/043154.
47. Wang et al., International Patent Application No. PCT/US2016/044287.
48. Wang et al., International Patent Application No. PCT/US2016/051755.

What is claimed is:

1. A system for performing simultaneous X-ray imaging and magnetic resonance imaging (MRI), the system comprising:
    an X-ray source;
    an X-ray detector for detecting X-rays from the X-ray source;
    a radio frequency (RF) coil;
    at least one gradient coil; and
    a magnetic field source for MR imaging, the magnetic field source comprising a first magnet ring and a second magnet ring disposed such that their radii are substantially parallel to each other, and a partial third magnet ring disposed between the first and second magnet rings in an axial direction substantially perpendicular to the radii of the first and second magnet rings such that the partial third magnet ring is not concentric to either of the first magnet ring and the second magnet ring;
    wherein the system is configured such that, during imaging of a subject:
        the X-ray source and X-ray detector are simultaneously rotated around the subject; and
        the magnetic field source is rotated around the subject.
2. The system of claim 1, wherein the system is configured such that, during imaging of a subject, the X-ray source, the X-ray detector, and the magnetic field source are all translated longitudinally along a region of interest of the subject.
3. The system of claim 1, wherein each of the first magnet ring, the second magnet ring, and the partial third magnet ring comprise a plurality of permanent magnets.
4. The system of claim 3, wherein the plurality of permanent magnets are arranged in a Halbach configuration.
5. The system of claim 3, wherein the plurality of permanent magnets are arranged in a magnet bar arrangement.

6. The system of claim 1, wherein each of the first magnet ring, the second magnet ring, and the partial third magnet ring comprise a plurality of magnet blocks.

7. The system of claim 6, wherein the partial third magnet ring has less magnet blocks than either of the first magnet ring and the second magnet ring.

8. The system of claim 6, wherein each of the first magnet ring and the second magnet ring comprise eight magnet blocks.

9. The system of claim 6, wherein each magnet ring is configured such that each of its magnet blocks has corresponding polarity to the magnet blocks in the same position on the other magnet rings.

10. The system of claim 1, wherein each of the first magnet ring, the second magnet ring, and the partial third magnet ring comprise a plurality of resistive magnet coils.

11. The system of claim 1, wherein each of the first magnet ring, the second magnet ring, and the partial third magnet ring comprise a plurality of solenoids.

12. The system of claim 11, wherein each solenoid is a Bitter plates solenoid.

13. The system of claim 11, wherein the X-ray source and the X-ray detector are both disposed in a bore of the solenoids.

14. The system of claim 11, wherein the system is configured such that the subject to be imaged is placed inside a bore of the solenoids.

15. The system of claim 11, wherein the RF coil is disposed between two solenoids, and wherein the system is configured such that the subject to be imaged is placed inside the RF coil.

16. The system of claim 11, wherein the X-ray source and the X-ray detector are both disposed outside the RF coil and outside bores of the solenoids.

17. The system of claim 11, wherein the X-ray source is disposed outside the RF coil and in a bore of a first solenoid of the plurality of solenoids, and the X-ray detector is disposed outside the RF coil and in a bore of a second solenoid of the plurality of solenoids.

18. The system of claim 1, wherein the magnetic field source generates a magnetic field with a maximum strength of 0.50 T or less.

19. The system of claim 1, further comprising a machine for reconstructing the image(s) of the subject to be imaged, the machine comprising at least one machine readable media having machine-executable instructions stored thereon for performing a method for reconstructing at least one image of the subject to be imaged, the method for reconstructing the at least one image of the subject to be imaged comprising:
   i) reconstructing X-ray computed tomography (CT) and MRI images using the simultaneous algebraic reconstruction technique with total variation (SART-TV) to obtain convex optimization equations;
   ii) combining structural coupling and compressive sensing techniques, in which each sub-image is represented by paired local X-ray CT-MRI structures to obtain convex optimization equations; and
   iii) solving the convex optimization equations from steps i) and ii).

20. The system of claim 19, wherein solving the convex optimization equations from steps i) and ii) comprises solving the convex optimization equations using a split-Bregman framework.

21. The system of claim 19, wherein step i) comprises using the following equations:

$$\min_{u_{CT}} \|u_{CT}\|_{TV}, \text{ s.t. } Mu_{CT} = f, \text{ and}$$

$$\min_{u_{MRI}} \|u_{MRI}\|_{TV}, \text{ s.t. } RFu_{MRI} = g,$$

where $u_{CT}$ and $u_{MRI}$ are respectively X-ray (e.g., X-ray CT) and MR images to be reconstructed, M is a system matrix in X-ray (e.g., X-ray CT) imaging, F denotes the Fourier transform, R is a sampling mask in the k-space, f and g are X-ray (e.g., X-ray CT) and MRI measurements, respectively, and $\|\cdot\|_{TV}$ denotes the TV transformation.

22. The system of claim 21, wherein step i) comprises using an artificial neural network to guide both X-ray CT and MIII reconstructions.

23. The system of claim 19, wherein step ii) comprises using the following equations:

$$\min_{u_{CT}} (1-\alpha)\|u_{CT}\|_{TV} + \alpha\|u_{CT} - u_{CT}^{est}\|_{TV}, \text{ s.t. } Mu_{CT} = f, \text{ and}$$

$$\min_{u_{MRI}} (1-\alpha)\|u_{MRI}\|_{TV} + \alpha\|u_{MRI} - u_{MRI}^{est}\|_{TV}, \text{ s.t. } RFu_{MRI} = g,$$

where $u_{CT}$ and $u_{MRI}$ are respectively X-ray (e.g., X-ray CT) and MR images to be reconstructed, M is a system matrix in X-ray (e.g., X-ray CT) imaging, F denotes the Fourier transform, R is a sampling mask in the k-space, f and g are X-ray (e.g., X-ray CT) and MIII measurements, respectively, $\|\cdot\|_{TV}$ denotes the TV transformation, $u_{CT}^{est}$ and $u_{MRI}^{est}$ are estimated images using the X-ray (e.g., X-ray CT)-MRI artificial neural network according to the corresponding X-ray (e.g., X-ray CT) and MRI images, respectively, $\alpha$ balances contributions from total variation and image similarity, respectively.

24. The system of claim 23, wherein step ii) comprises using an artificial neural network to guide both X-ray CT and MIII reconstructions.

25. The system of claim 1, wherein the X-ray detector is a flat detector array.

26. The system of claim 1, wherein the at least one gradient coil comprises an X gradient coil, a Y gradient coil, and a Z gradient coil.

27. The system of claim 1, wherein the magnetic field source is disposed such that no portion of it is interposed between the X-ray source and the X-ray detector.

28. A method for performing simultaneous X-ray imaging and magnetic resonance imaging (MRI), the method comprising: providing a subject to be imaged; and using the system of claim of 1 to perform simultaneous X-ray imaging and MRI on the subject.

* * * * *